United States Patent
Pozniak

(10) Patent No.: US 10,568,598 B2
(45) Date of Patent: Feb. 25, 2020

(54) FLUOROSCOPY SYSTEM RESOLVING SLOWLY EVOLVING CONDITIONS

(71) Applicant: Wisconsin Alumni Research Foundation, Madison, WI (US)

(72) Inventor: Myron A. Pozniak, Waunakee, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 773 days.

(21) Appl. No.: 15/197,081

(22) Filed: Jun. 29, 2016

(65) Prior Publication Data

US 2018/0000437 A1 Jan. 4, 2018

(51) Int. Cl.
*A61B 6/00* (2006.01)

(52) U.S. Cl.
CPC ............ *A61B 6/463* (2013.01); *A61B 6/4441* (2013.01); *A61B 6/487* (2013.01); *A61B 6/54* (2013.01)

(58) Field of Classification Search
CPC ....... A61B 6/4441; A61B 6/463; A61B 6/487; A61B 6/54
See application file for complete search history.

(56) References Cited

U.S. PATENT DOCUMENTS

| | | | | |
|---|---|---|---|---|
| 4,719,644 A * | 1/1988 | Herzog | ................... | H04N 7/012 378/98.2 |
| 5,861,865 A * | 1/1999 | Anand | ................... | A61B 5/055 174/350 |
| 2002/0006184 A1 * | 1/2002 | Katoh | ................... | A61B 6/02 378/196 |
| 2003/0091154 A1 * | 5/2003 | Crain | ..................... | A61B 6/107 378/197 |
| 2004/0116804 A1 * | 6/2004 | Mostafavi | .............. | A61B 5/113 600/428 |
| 2006/0074286 A1 * | 4/2006 | Miller | .................... | A61B 6/032 600/407 |
| 2007/0195935 A1 * | 8/2007 | Vermeulen | ........... | A61B 5/0046 378/145 |
| 2008/0317305 A1 * | 12/2008 | Cover | ...................... | G06T 5/50 382/128 |
| 2009/0110252 A1 * | 4/2009 | Baumgart | .............. | A61B 6/481 382/130 |
| 2009/0201841 A1 * | 8/2009 | Tachikawa | ........... | G01N 23/223 378/44 |
| 2012/0027178 A1 * | 2/2012 | Mabini | .................. | A61B 6/461 378/98 |
| 2012/0201432 A1 * | 8/2012 | Neidert | .................. | A61B 5/066 382/128 |
| 2013/0094626 A1 * | 4/2013 | Kobayashi | ............. | A61B 6/032 378/19 |
| 2013/0156154 A1 * | 6/2013 | Watanabe | .............. | A61B 6/022 378/42 |
| 2014/0039305 A1 * | 2/2014 | Wenderow | ............... | A61B 6/12 600/424 |
| 2018/0271472 A1 * | 9/2018 | Ercan | ..................... | A61B 6/467 |

* cited by examiner

*Primary Examiner* — Chih-Cheng Kao
(74) *Attorney, Agent, or Firm* — Boyle Fredrickson S.C.

(57) ABSTRACT

A fluoroscopy machine allows programming of a frame rate in the range of multiple seconds per frame and then displays the images at a higher rate in a loop in the radiological theater so as to impart an improved sense of motion to a human observer of a slow physiological processes captured by fluoroscopic studies.

17 Claims, 5 Drawing Sheets

FLUOROSCOPY SYSTEM RESOLVING SLOWLY EVOLVING CONDITIONS

STATEMENT REGARDING FEDERALLY SPONSORED RESEARCH OR DEVELOPMENT

Cross Reference to Related Application

Background of the Invention

The present invention relates to x-ray fluoroscopy systems and the like and in particular to an x-ray fluoroscopy system providing cane capabilities specifically resulting in superior analysis of slowly evolving conditions.

X-ray fluoroscopy provides real-time x-ray imaging of a patient such as can be important in many interventional procedures (e.g., catheterizations) and in studies of changes in the body over a short period of time (for example, the movement of a contrast agent through the heart or evaluation of the swallowing mechanism). Original fluoroscopy Machines essentially used a continuous x-ray exposure: however, current machines can capture a succession of short, pulsed, low-dose exposures with an image intensifier tube and preserved electronically resulting, in a short moving image of the area of interest.

In a typical x-ray fluoroscopy system, an x-ray tube is positioned on a gantry opposite an image intensifier and the gantry is movable to position a patient for x-ray acquisition. An electronic camera incorporated into the image intensifier allows the received x-ray image to be displayed on a standard electronic display and stored, for example, as a digital file. The electronic display may hold each acquired image persistently until the next image is obtained to provide the appearance of continuous viewing at frame rates ranging anywhere from 3 to 30 frames per second. Lower frame rates provide a corresponding reduction in patient exposure but with a loss of time resolution and a decrease quality of real time imaging of rapidly moving structures.

A fluoroscopy machine may provide for cine recording capabilities in which successive images are recorded so that they may be played back in the manner of a movie for later analysis. For example, a series of fluoroscopic images obtained at a high frame rate (e.g., 30 frames per second) can capture the swallowing of a contrast agent and then be played back for review to analyze possible swallowing disorders.

For certain studies, for example, involving contrast agents moving through the bowel, it may be desirable to monitor the patient over an extended length of time, from several minutes to several hours. Continuous cine operation of the fluoroscopy machine during such extended periods is generally avoided and instead the radiologist may opt to take periodic images manually to monitor the procedure and the progress of the contrast.

In some cases, for example, when it is desired to locate a perforation of the bowel, such randomly timed manual acquisitions may miss a critical moment of contrast agent escape from the bowel such as may occur over a period of a few seconds in the middle of contrast transit through the gut during an otherwise lengthy procedure. In other cases, such a randomly timed irregular manual acquisition can make it difficult to obtain an intuitive understanding of the dynamics of the observed process. That is, the radiologist, observing the last few images may capture only an imperfect understanding of the timing of the movement of contrast agent through the bowel, or its precise point of escape if leaking, for example. This in turn can hamper the radiologist's ability to properly time the next exposure, compounding an inability to capture and/or understand the slowly moving process. Additionally if a large amount of contrast escapes before initial detection, it may obscure the underlying source of leak hampering anatomic definition required by the surgical team considering intervention.

SUMMARY OF THE INVENTION

The present invention provides a fluoroscopy machine that can operate in cine mode with acquisition frame rate measured not in frames per second but seconds per frame. By displaying the slowly acquired data at a higher frame rate in the radiological suite, a "time-lapse" sequence of images in a real-time format can be provided to the radiologist. This not only presents a slowly evolving process at a more interpretable time-scale but allows the acquisition, of a sufficiently long segment at relatively low dose to ensure that a critical moment in the process is not overlooked during gaps in imaging.

Specifically then, the present invention, in one embodiment, provides a fluoroscopy machine having a gantry system holding an x-ray source operable to provide discrete x-ray exposures according to a control signal and an image intensifier opposite the x-ray source to receive x-rays from the x-ray source during the discrete x-ray exposures and to provide image data. The fluoroscopy machine farther includes input for receiving instructions from a fluoroscopy machine user and a display for receiving the image data. A fluoroscopy control circuit communicates with the x-ray source, image intensifier, and display and operating to: (a) receive instructions through the input identifying an acquisition frame rate in a range providing multiple seconds between each frame, (b) control the x-ray source and image intensifier to obtain a set of time-ordered images at separated acquisitions at the acquisition frame rate; and (c) provide a looping display on the display of the set of time-ordered images in sequence according to a display rate different (accelerated) from the acquisition frame rate.

It is thus a feature of at least one embodiment of the invention to provide the radiologist with an improved, near real-time understanding of slowly evolving physiological processes when monitored by fluoroscopy imaging. The rolling, accelerated playback of the acquired data aids the radiologist in making decisions about the ongoing imaging including determining whether sufficient data has been collected or whether the parameters for the data collection need to be changed, for example, changing the frame rate, adding additional contrast or adjusting the region of interest. The regular timing of image acquisition helps ensure that critical information is captured for later study and interpretation.

The fluoroscopy control circuit may further receive a loop length from the input to provide a looping display of a subset of the acquired time-ordered images limited in length by the loop length and terminating at a latest time order image.

It is thus a feature of at least one embodiment of the invention to automatically present the radiologist the latest data plus enough historical context to provide for a sequence of images conveying motion.

The fluoroscopy control system may operate to receive frame acquisition instructions by an operator during the obtaining of the time-ordered images to change the acquisition frame rate during the obtaining of the time-ordered images.

It is thus a feature of at least one embodiment of the invention to permit the radiologist to change the time granularity of the acquisitions based on the insight provided by the rolling display of recently acquired image data.

The gantry may include at least one electrically controlled actuator to reposition the gantry, and the fluoroscopy control system may further receive reposition instructions and communicate with the gantry to incrementally reposition the gantry according to the reposition instructions in between each acquisition.

It is thus a feature of at least one embodiment of the invention to permit a tracking of slowly evolving phenomenon in the patient through a movement of the gantry on an automatic basis keyed to the acquisitions.

The fluoroscopy control system may operate to receive a start location and stop location of the gantry, and the reposition instructions may provide a constant average velocity of gantry movement independent of acquisition frame rate.

It is thus a feature of at least one embodiment of the invention to provide a perceptively smooth movement in the resulting display of the acquired data with respect to real time and independent of acquisition rate that assists in understanding the data.

The fluoroscopy control system may further operate to receive an override instruction overriding the repositioning instructions with an override position causing the gantry to move to the override position.

It is thus a feature of at least one embodiment of the invention to permit the radiologist to respond to the improved information provided by the looping display to reposition the gantry at any time.

In one embodiment, the fluoroscopy system may further receive spot film instructions to: (i) record a location of the gantry, (ii) pause the obtaining of the time-ordered images to receive repositioning instructions through the input; (iii) communicate with the gantry to reposition the gantry for obtaining a spot film; (iv) reposition the gantry at the recorded location; and (v) resume obtaining the time-ordered images.

It is thus a feature of at least one embodiment of the invention to permit the acquisition of detailed spot films in between serial acquisitions with minimal disruption to the information obtained by the low dose serial acquisitions.

The fluoroscopy machine may further provide one of an audio and/or visual output perceivable by a patient positioned between the x-ray tube and the image intensifier providing a warning of an x-ray acquisition of the separated acquisitions at a predetermined time interval proceeding acquisition.

It is thus a feature of at least one embodiment of the invention to provide an automatic system of alerting the patient and radiologist to the imminent acquisition of x-ray data that can be separated by many seconds.

The warning may indicate a length of the predetermined time interval preceding the acquisition.

It is thus a feature of at least one embodiment of the invention to allow the patient and radiologist to anticipate the acquisition of fluoroscopy data, for example, to minimize motion.

In this regard the fluoroscopy machine may provide audio and/or visual output perceivable by a patient positioned between the x-ray tube and the image intensifier and wherein the fluoroscopy control system further provides breath hold instructions at each acquisition using the one of an audio and visual output. The breath hold instructions may precede each acquisition of the separated acquisitions and instruct the patient to hold his or her breath and may immediately follow each acquisition of the separated acquisitions and instruct the patient to breathe normally.

It is thus a feature of at least one embodiment of the invention to provide automatic repeated breath hold instructions to the patient to simplify the acquisition of multiple images greatly exceeding the duration of a single breath hold.

It is thus a feature of at least one embodiment of the invention to provide automatic repeated breath hold instructions to the patient to situate anatomy near the diaphragm at a similar level among exposures, thereby minimizing respiratory motion artifact.

The fluoroscopy machine may include a proximity sensor for sensing the presence of the radiologist and obtaining acquisitions only if the radiologist is present at a location for viewing the fluoroscopy machine and patient.

It is thus a feature of at least one embodiment of the invention to ensure proper supervision of the patient in the context of automatic or semiautomatic x-ray exposures.

The proximity sensor may be selected from the group consisting of a pressure mat, a radio link, a Bluetooth link, and/or a physically, operated electrical switch.

It is thus a feature of at least one embodiment of the invention to provide radiologist supervision with minimal distraction to the radiologist.

The fluoroscopy machine may include a memory system for storing data of the separated acquisitions for later review.

It is thus a feature of at least one embodiment of the invention to permit the preservation of the acquired data for future study and documentation.

These particular objects and advantages may apply to only some embodiments falling within the claims and thus do not define the scope of the invention.

DETAILED DESCRIPTION OF THE PREFERRED EMBODIMENT

Figure 1:
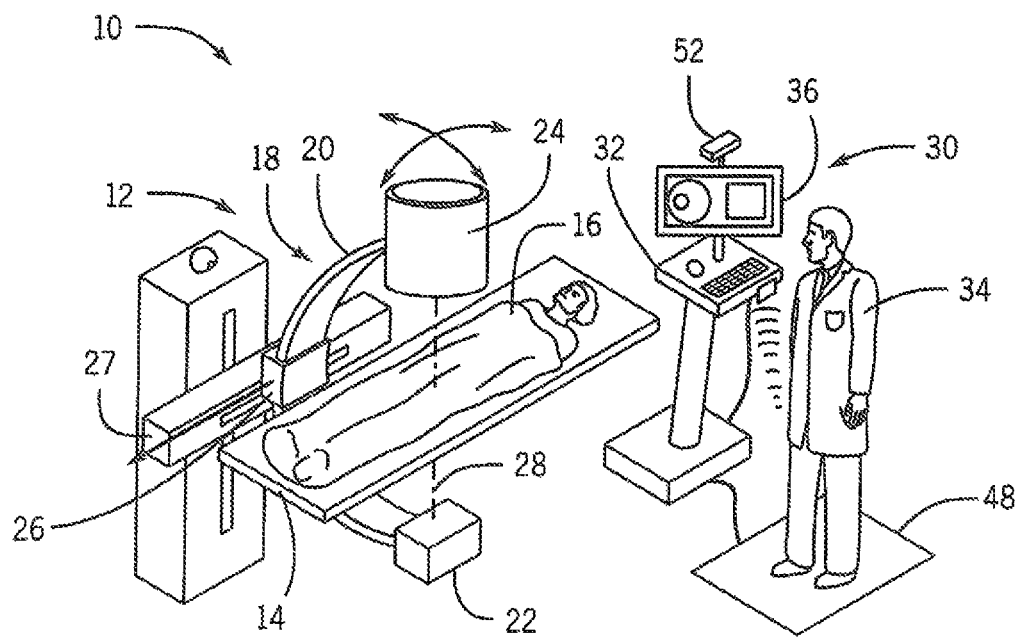
FIG. 1 is a perspective view of a simplified fluoroscopy machine suitable for use with the present invention providing an x-ray room monitor for viewing cine images.

Referring now to FIG. 1, a fluoroscopy suite 10 may hold a fluoroscopy machine 12 providing a patient table 14 supporting a patient 16 near a gantry 18. The gantry 18, in one embodiment, may provide for a C-arm 20 having opposed ends, one and holding an x-ray source 22 and the other and holding an image intensifier 24 in opposition to the x-ray source 22 along an axis 28 directed through the patient 16 for imaging the patient 16.

The C-arm 20 may be supported between its opposed ends in a collar 26 so that an axis 28 between the x-ray source 22 and image intensifier 21 may be changed in angle about an inferior-superior axis of the patient 16 by movement of the C-arm 20 through the collar 26 or about a lateral angle by angulation of the collar 26 with respect to the track 27. These movements may be effected by associated motorized actuators to be discussed below. In addition, the collar 26 may be held on a track 27 allowing the collar 26 to be moved laterally (parallel to the patient's superior-inferior axis) to change a region of imaging.

Figure 2:
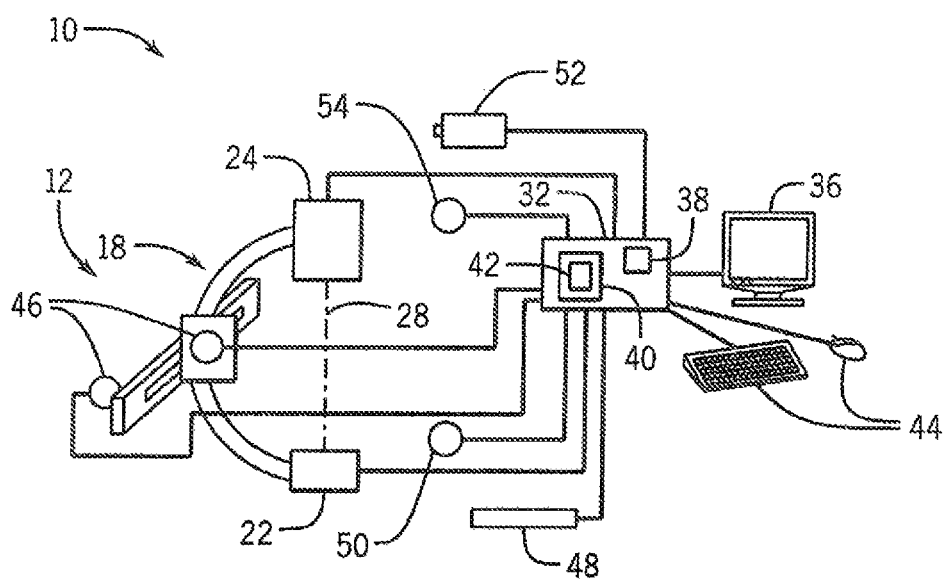
FIG. 2 is a block diagram of the principal elements of the fluoroscopy machine of FIG. 1 including a computer controller.

Referring also to FIG. 2, the fluoroscopy machine 12 may include a control station 30 providing a control computer 32 for control of the fluoroscopy machine 12 by a healthcare professional 34. In this regard, the control computer 32 may communicate with an electronic display 36 for concurrent display of fluoroscopic images to the healthcare professional 34 and with one or more user input devices 44 such as a mouse and keyboard as is generally understood in the art.

The control computer 32 further provides for electrical interfaces that allow for control of the image intensifier 24 including the receipt of x-ray image data from that image intensifier 24 and control of the x-ray source 22 to activate the x-ray source 22 and to control imaging parameters such as exposure duration, voltage and current provided to an x-ray tube according to a desired imaging protocol.

The control computer 32 may further communicate with motorized actuators 46 associated with the gantry 18 to provide the above-described angulation of the axis 28 and lateral movement of that axis 28.

The present invention may optionally also provide for one or More proximity sensors such as a pressure mat 48 or radio sensor, for example, the latter using low-power Bluetooth sensing communicating with a tag worn by the healthcare professional 34, or an RFID tag reader reading a tag worn by the healthcare professional 34 to detect the presence of the healthcare professional 34 in a supervisory capacity. In one embodiment the control computer 32 may communicate with an electronic camera 52 such as may provide for remote observation of the patient and fluoroscopy machine 12 in a signal from the healthcare professional 34 provided through a remote display associated with the electronic camera 52, for example, by a switch activated by the healthcare professional 34, which may provide for the proximity signal.

The control computer 32 may further communicate with a patient communication device 54, for example, in the form of a lighted sign, display and or audio speaker system that can give the patient 16 and healthcare professional 34 warnings about the imminent activation of the x-ray source 22 and/or automatic breath hold instructions as will also be discussed.

Figure 3:
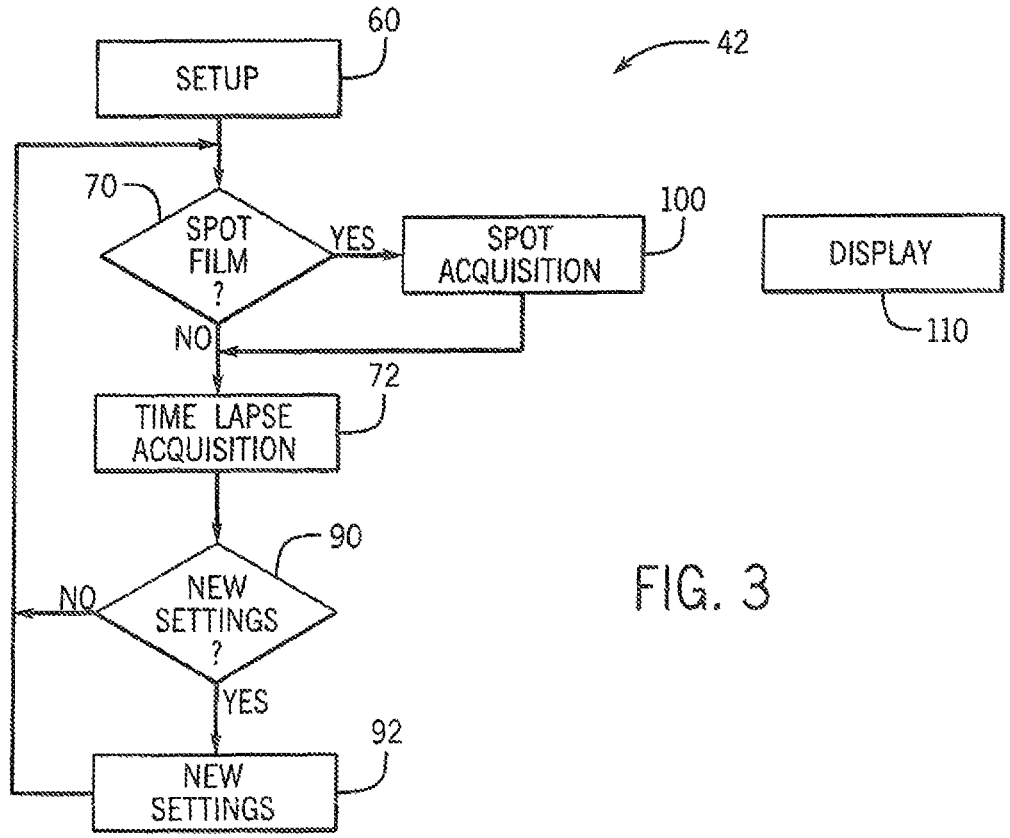
FIG. 3 is a flowchart of the principal components of a program executable by the computer controller of FIG. 2 and providing the cine acquisition and display.

Generally, the control computer 32 may include one or more processors 38 communicating with a memory 40, the latter holding a stored program 42 providing specific control of these interconnected features. Referring now also to FIG. 3, this program 42 executed by the control computer 32 may initially present the user with the opportunity to set up the parameters of a fluoroscopy acquisition, for example, using the interface elements of the control computer 32 and as indicated by process block 60.

Figure 4:
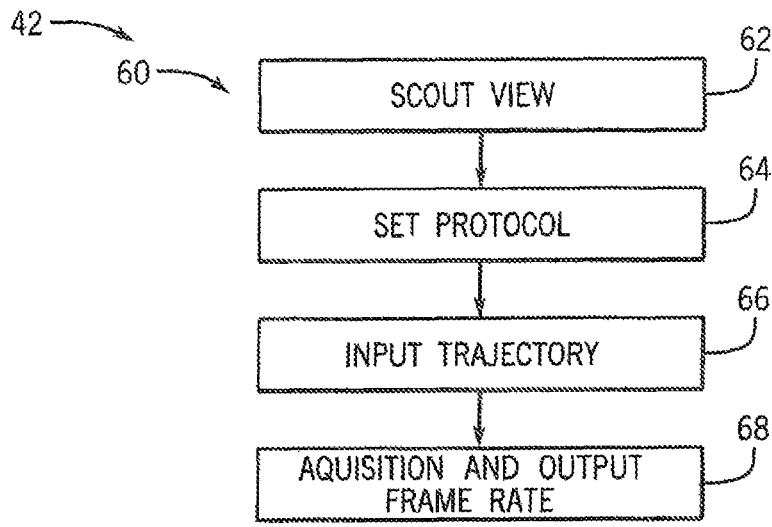
FIG. 4 is a detailed flowchart of a set up procedure of the program of FIG. 3.

As shown in FIG. 4, the set up process may begin as indicated by process block 62 with the obtaining of a "scout view" providing a large field of view of the patient defining a region in which the fluoroscopic sequence will be acquired. This scout view scan may be the basis for other settings in the set up process block 60, for example, defining a trajectory of gantry motion as will be discussed below.

At succeeding process block 64, the x-ray exposure protocols, exposure duration, tube voltage, and current may be set. At this time the total length of the study or the total number of exposures and collected images may be set.

At process block 66 the healthcare professional 34 may enter information defining a trajectory of the gantry 18 in angle, and offset during the acquisition of a fluoroscopic sequence. In one embodiment, the user may locate a starting position and ending position of a fluoroscopic sequence to be acquired, for example by maneuvering the gantry 18 to each of these locations. Alternatively this information may be entered manually and/or marked on the scout view image. A number of discrete locations at which exposures will be taken may be determined by dividing the described movement according to the total length of the study or number of exposures defined in process block 64.

Normally the automatic control of the gantry 18 will be such as to provide a constant average speed of movement of the gantry 18 between the starting position and stopping position using discrete repositioning events in between each x-ray exposure when the gantry 18 is not moving. Alternatively, a trajectory may be associated with changing speeds of movement and angulation of the C-arm 20. As will be discussed further below, the trajectory may be modified at any time by the healthcare professional 34 and may be interrupted to obtain spot films and the like.

At subsequent process block 68, starting acquisition frame rates and output frame rates may be entered by the healthcare professional 34. The acquisition frame rate will define a separation in time between successive exposures of the patient and will include frame rates that have multiple seconds between frames, for example, 3 to 10 seconds between frames, but may also provide for standard cine frame rates providing multiple frames per second as well as much lower frame rates.

In contrast, the output frame rate will be the frame rate at which the acquired images will be output on the display 36 in the radiology suite 10 as will be discussed below. Typically this output rate will be dictated by a desire to avoid "flicker" or "stuttering" being a noticeable blinking or stopping between each frame such as interferes with the perception of continuous motion. For example, the output rate may range between one and 30 frames per second and will typically be in excess of 10 frames per second. Nevertheless an arbitrarily wide range of output rates may be selected including frame rates which change as a function of the particular image of the sequence.

At process block 68, a maximum loop duration may be set or default value may be provided defining a maximum loop of images that will be displayed before repeating as will also be described below.

Referring again to FIG. 3, after completion of the set up process, assuming no spot film is requested (as determined by decision block 70) the program 42 proceeds to process block 72 to begin a time-lapse acquisition of fluoroscopic images using the trajectory and acquisition rate entered during the set up process of process block 60.

Figure 5:
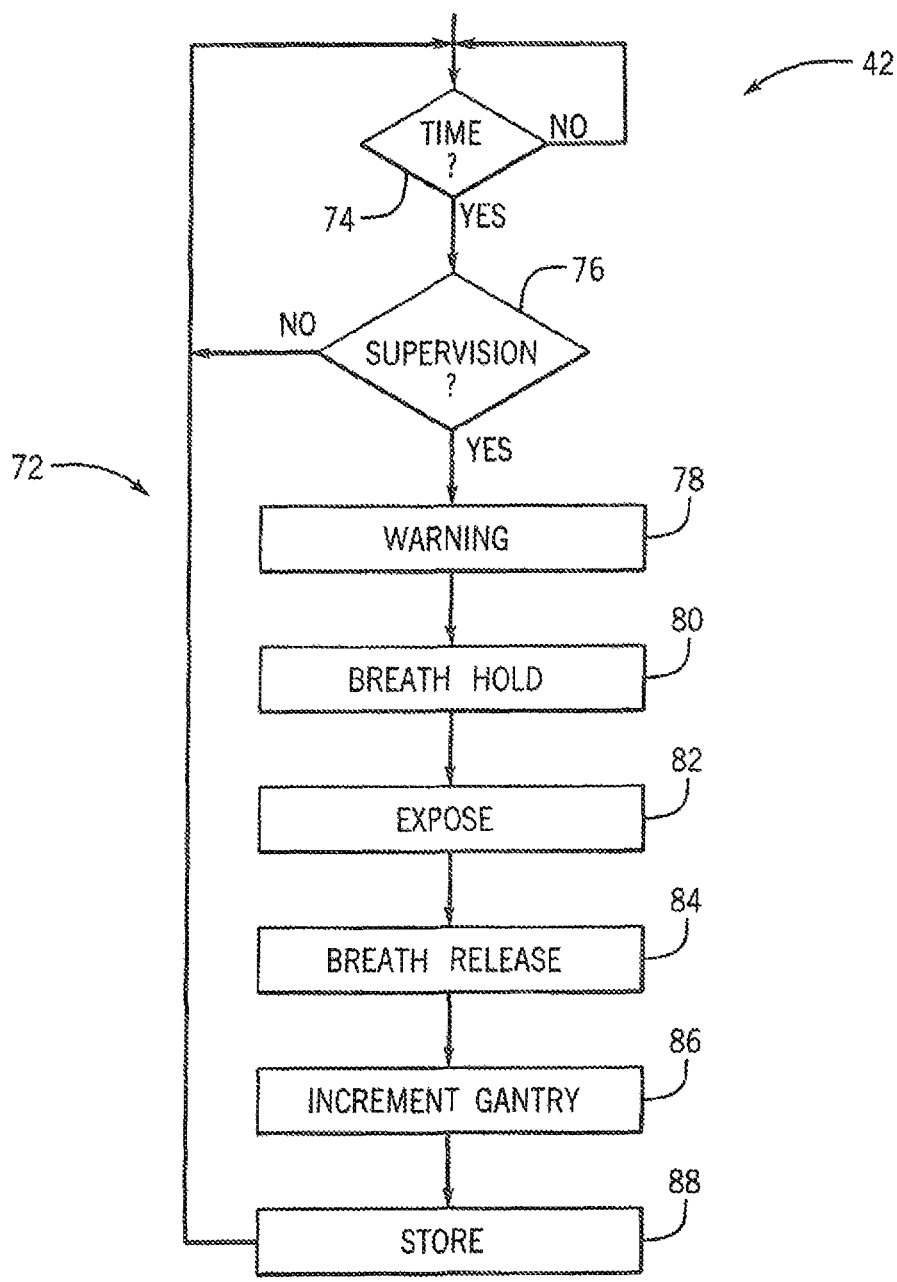
FIG. 5 is a detailed flowchart of a time-lapse acquisition procedure of the program of FIG. 3.

Referring to FIG. 5, the time-lapse acquisition of process block 72 is synchronized by a time measurement indicated by decision block 74 which determines the elapsed time since a previous acquisition of a fluoroscopic image and a desired series of fluoroscopic images. When that, elapsed time exceeds the time between acquisitions required by the preset acquisition frame rate, program 42 proceeds to process block 76.

At process block 76 a determination is made as to whether the fluoroscopy machine 12 and patient 16 are being supervised by the healthcare professional 34 as may be required by regulations or practice guidelines. This supervision may be established, for example, by an entry by a healthcare professional 34 on the keyboard of the control computer 32 or the pressing and holding of an electrical switch, or may be established automatically or semi-automatically, for example, by the healthcare professional 34 standing on the pressure mat 48 or being in the proximity of the control computer 32. In this latter example, the proximity may be measured by any of the proximity sensors 50 discussed above. In some options, supervision may be provided through remote viewing by the healthcare professional 34, for example, through camera 52. In this case supervision may be established using a remote signal provided by the healthcare professional 34 through a remote monitor communicating with camera 52.

If proper supervision is established, then at process block 78, a warning indicator is provided, for example, to the patient 16 through patient communication device 54 or on the display 36. This warning prevents unexpected activation of the x-ray machine and may be a simple tone or light or may provide the communication of a number of seconds or the like for an x-ray exposure that will be initiated, for example, using a countdown.

At succeeding process block 80, breath hold instructions may be provided to the patient, for example, by an audible message indicating that the patient should take a moderate breath and then hold his or her breath. At process block 82, an x-ray exposure is initiated at the current gantry 18 position using the parameters provided in the set up steps of process block 60. Breath release instructions are then provided to the patient 16 at process block 84 informing the patient 16 that they may breathe normally.

At process block 86, the gantry 18 may be repositioned according to the trajectory defined at process block 66 to stop at the next location for an exposure. At process block 88, the acquired image from the image intensifier 24 resulting from the exposure of process block 82 is stored as part of a sequence of images each ordered according to the order of acquisition and tagged with a time and technique. This stored data may be reviewed later using the control computer 32 or other computer by playing the data in sequence at various playback rates or "scrubbing" the data forward and backwards to provide animation. In addition, individual frames of the data may be reviewed.

Referring again to FIG. 3, if the total length of the acquisition has not been reached (measured in time or exposures), the program 42 may then check for new settings from the healthcare professional 34, for example, frame rates per decision block 90, and if there are no new settings return to the top of process block 72 and repeat this process at the next frame interval.

If at decision block 90 there are new settings desired by the healthcare professional 34 during the scan, the program proceeds to process block 92 to input those new settings in the manner of process block 60 and then returns to the top of decision block 70. These new settings may include, for example, a change in acquisition rate or in the endpoint of the trajectory. In such circumstances, a new trajectory may be calculated with discrete exposure locations according to the new inputs. Generally the new exposure locations are selected so as to preserve average speed of the gantry 18 before and after the new settings if the endpoint of the trajectory has not been changed.

Figure 6:
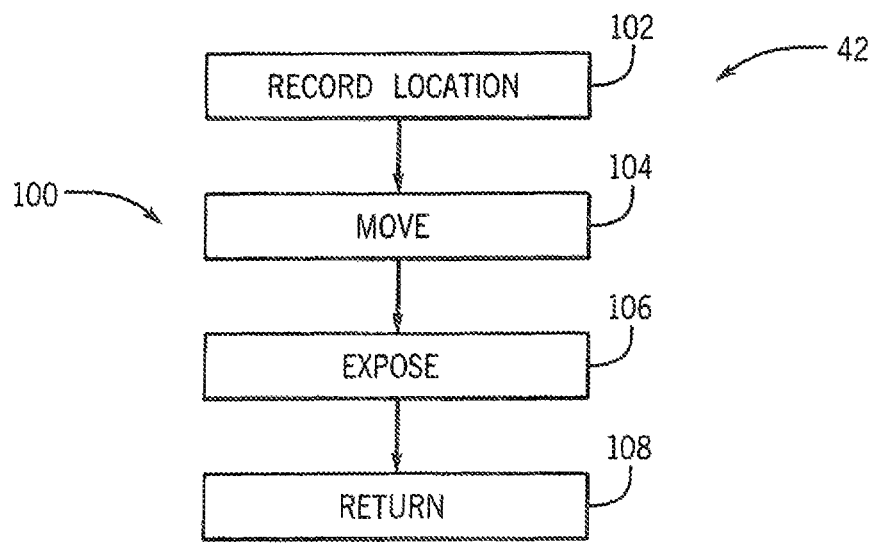
FIG. 6 is a plot of gantry movement synchronized to cine acquisition showing adjustment of frame rate and motion parameters during the acquisition.

Referring now to FIG. 6, an initial trajectory of the gantry 18 may provide, for example, a trajectory 93 at a first acquisition frame rate 94. Although this trajectory 93 is shown as a simple one-dimensional movement, it should be generally understood that this trajectory may be in multiple dimensions of angulation and translation.

At time $t_1$ the attending healthcare professional 34 may change the frame rate to a faster acquisition rate 96 to provide for higher time resolution, based on the healthcare professional's anticipation of an event that will require additional accuracy (greater temporal resolution) in the recording. The time-linear trajectory 93 of the gantry 18, if not changed during the new settings of process block 92, will continue at the same time rate unaffected by the change in acquisition time.

At time $t_2$, the healthcare professional 34 may enter a new trajectory speed, for example, by changing the study time or endpoint. In this example, the healthcare professional 34 has stopped the gantry 18 to obtain multiple fluoroscopic images over time at a given location. Again this change in the trajectory may operate independently of the acquisition rate 96.

Referring to FIGS. 3 and 6, at decision block 70, at any time during the acquisition of the sequence of fluoroscopic images, the healthcare professional 34 may indicate a desire to make a spot film to provide additional detail of the patient at that instant in time. This request which may be entered through the control computer 32 causes the program 42 to proceed to process block 100.

Figure 7:
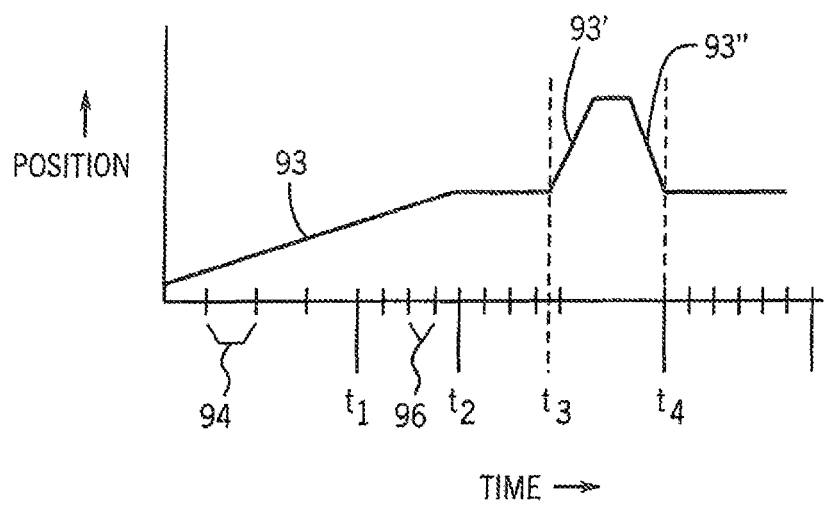
FIG. 7 is a detailed flowchart of a spot acquisition procedure of the program of FIG. 3.

Referring also to FIG. 7, at process block 100, the current location of the gantry 18 is stored per process block 102 and the gantry 18 moved, for example, by healthcare professional 34 control per process block 104 to the location where the spot film will be acquired. This movement is shown in FIG. 6 by new trajectory 93'. During this spot film acquisition, ongoing acquisition of the sequence of fluoroscopic images is suspended.

At process block 106, the healthcare professional 34 makes the exposure of the spot film. Following, this exposure, as indicated by process block 108, the control computer 32 executing the program 42 may return the gantry 18 to its previous location as indicated by trajectory 93" to resume acquisition of the fluoroscopic sequence. Depending on the length of time required to obtain the spot film, one or more scheduled fluoroscopic acquisitions at the acquisition rate 96 may have been skipped. These missing images may be indicated by black frames in the displayed image to preserve time continuity or may be simply omitted, causing a jump in time at the point where these images would have been displayed. In one embodiment, upon completion of the spot film, the gantry 18 may be returned to a position where it would have been if the acquisition process had not been interrupted. In any case, acquisition of a regular sequence of fluoroscopic images then proceeds until the time or image limit previously entered by the healthcare professional 34 in the set up process block 60.

Figure 8:
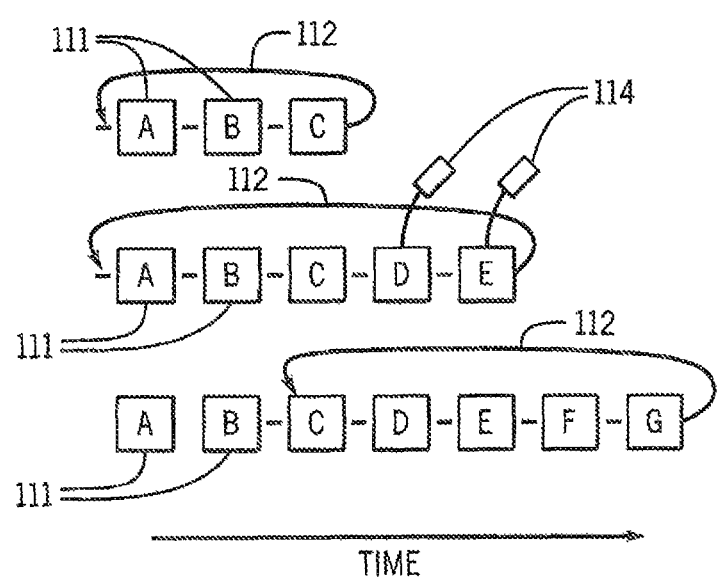
FIG. 8 is a schematic representation of a rolling cine display visible in the radiological suite.

Referring now to FIGS. 3 and 8, during the acquisition of a sequence of fluoroscopic images indicated at process block 72, a display routine 110 operates in parallel, to display currently acquired image data 111 of that sequence of fluoroscopic images. As shown in FIG. 8 this display process will generally loop as indicated by loop arrow 112 through a sequence of fluoroscopic images acquired at process block 82 of FIG. 5 up to a maximum number of those images described in the set up of process block 60. Each loop will present on the display 36 a movie-like presentation of the acquired images in a greatly accelerated manner such as provides a perception of motion to a process that may be too slow for motion to be directly perceived. Repeating the loop provides an essentially continuous representation of the motion revealed by the fluoroscopic images for review by the healthcare professional 34.

Normally the length of the loop will be truncated so as to provide easy comprehension of the physiological activity immediately preceding the current state of the patient. This loop length may be set during the set up described with respect to process block 60. For example, if the set up describes a loop consisting of five sequential fluoroscopic images (greatly reduced in number for the purpose of this explanation), if three fluoroscopic images have been obtained and denoted A, B, and C, the display of process block 110 will loop through each of those images A, B, and C at the display rate (set at process block 60 but which may be adjusted at any time by the healthcare professional 34). This loop allows the healthcare professional 34 to immediately see the progress, of any contrast material on the fluoroscopic scan with the newly accessible dimension of accelerated motion that would otherwise be difficult to perceive through a real time display of the image data 111 at its acquisition frame rate.

As additional images 111, (e.g., five frames denoted A-E) are acquired, the length of the loop may be increased up to the preset maximum level here shown as five frames. When seven frames have been acquired (indicated by images A-G), only the most recently acquired frames (C-G) will be part of the loop. In this way the most recent data is always displayed together with the recent history of that recent image to provide context.

As each image data 111 is acquired, the image data 111 may be tagged, for example, by a tag 114 with data entered by the healthcare professional 34 at the control computer 32, for example, including volumes of contrast infused into the patient at that time. Alternatively this information may be automatically extracted from an infusion pump. This tag 114 may be accessed at any time by the physician reviewing the images 111 to provide additional context for the images presented.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to, mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a computer" and "a processor" or "the microprocessor" and "the processor," can be understood to include one or more processors that can communicate in a stand-alone and/or a distributed environment(s), and can thus be configured to communicate via wired or wireless communications with other processors, where such one or more processor can be configured to operate on one or more processor-controlled devices that can be similar or different devices. In particular the control computer described above may be distributed among multiple processing machines. Furthermore, references to memory, unless otherwise specified, can include one or more processor-readable and accessible memory elements and/or components that can be internal to the processor-controlled device, external to the processor-controlled device, and can be accessed via a wired or wireless network.

Physical operation of a switch refers to using one's hand or foot or the like to activate the switch.

It is specifically intended that the present invention not be limited to the embodiments and illustrations contained herein and the claims should be understood to include modified forms of those embodiments including portions of the embodiments and combinations of elements of different embodiments as come within the scope of the following claims.

What I claim is:

1. A fluoroscopy machine comprising:
    a gantry system holding:
        (a) an x-ray source operable to provide discrete x-ray exposures according to a control signal; and
        (b) an image intensifier opposite the x-ray source to receive x-rays from the x-ray source during the discrete x-ray exposures and to provide image data;
    an input for receiving instructions from a fluoroscopy machine user;
    a display for receiving the image data; and
    a fluoroscopy control circuit communicating with the x-ray source, image intensifier, and display and operating to:
        (a) receive instructions through the input identifying an acquisition frame rate in a range providing multiple seconds between each frame;
        (b) control the x-ray source and image intensifier to acquire a set of time-ordered images at separated acquisitions at the acquisition frame rate and including a latest time ordered image being the last image acquired;
        (c) provide a looping display on the display of the set of time-ordered images in sequence according to a display rate different from the acquisition frame rate and terminating at the latest time ordered image;
        (d) control the x-ray source and image intensifier to acquire a new image added to the set of time-ordered images and representing a new latest time-ordered image being the last image acquired in the set of time-ordered images different from the latest time ordered image;
        (e) provide an updated looping display on the display of the set of time-ordered images in sequence according to the display rate different from the acquisition frame rate with the latest time-ordered image being the new latest time-ordered image; and
        (f) repeat steps (d) and (e).

2. The fluoroscopy machine of claim 1 wherein the fluoroscopy control circuit further receives a loop length from the input to provide a looping display of a subset of the acquired time-ordered images limited in length by the loop length.

3. The fluoroscopy machine of claim 1 wherein the acquisition frame rate varies between two and thirty seconds per frame.

4. The fluoroscopy machine of claim 1 wherein the acquisition frame rate varies between one and thirty frames per second.

5. The fluoroscopy machine of claim 1 wherein the fluoroscopy control system operates to receive frame acquisition instructions by an operator during the obtaining of the time-ordered images to change the acquisition frame rate during the obtaining of the time-ordered images.

6. The fluoroscopy machine of claim 1 wherein the gantry includes at least one electrically controlled actuator to reposition the gantry and wherein the fluoroscopy control system further receives reposition instructions and communicates with the gantry to reposition the gantry according to the reposition instructions in between each acquisition.

7. The fluoroscopy machine of claim 6 wherein the fluoroscopy control system operates to receive a start location and stop location of the gantry and the reposition instructions provide a constant average velocity of gantry movement independent of acquisition frame rate.

8. The fluoroscopy machine of claim 6 wherein the fluoroscopy control system operates to receive an override instruction overriding the reposition instructions with an override position causing the gantry to move to the override position.

9. The fluoroscopy machine of claim 1 wherein the fluoroscopy system further receives spot film instructions and operates to:
(i) record a location of the gantry;
(ii) pause the acquisition of the time-ordered images to receive repositioning instructions through the input;
(iii) communicate with the gantry to reposition the gantry for obtaining a spot film;
(iv) reposition the gantry at the recorded location; and
(v) resume acquisition of the time-ordered images.

10. The fluoroscopy machine of claim 1 further providing one of an audio and visual output perceivable by a patient positioned between the x-ray source and the image intensifier providing a warning of an x-ray acquisition of the separated acquisitions at a predetermined time interval preceding acquisition.

11. The fluoroscopy machine of claim 10 wherein the warning indicates a length of the predetermined time interval preceding the acquisition.

12. The fluoroscopy machine of claim 10 further providing one of an audio and visual output perceivable by a patient positioned between the x-ray source and the image intensifier and wherein the fluoroscopy control system further provides breath hold instructions at each acquisition using the one of an audio and visual output.

13. The fluoroscopy machine of claim 12 wherein the breath hold instructions precede each acquisition of the separated acquisitions instructing the patient to hold his or her breath and follow each acquisition of the separated acquisitions instructing the patient to breathe normally.

14. The fluoroscopy machine of claim 1 further including a proximity sensor for sensing a presence of a fluoroscopy machine operator and obtaining acquisitions only if the fluoroscopy machine operator is present at a location for viewing the fluoroscopy machine and patient.

15. The fluoroscopy machine of claim 14 wherein the proximity sensor is selected from the group consisting of a pressure mat, a radio link, and a physically operated electrical switch.

16. The fluoroscopy machine of claim 1 further including a memory system for storing data of the separated acquisitions for later review.

17. The fluoroscopy machine of claim 16 wherein the later review includes an ability to provide a movie-type display of the set of time-ordered images in sequence according to display rate controlled by an operator.

* * * * *